United States Patent [19]
Chien et al.

[11] Patent Number: 5,250,022
[45] Date of Patent: Oct. 5, 1993

[54] IONTOTHERAPEUTIC DEVICES, RESERVOIR ELECTRODE DEVICES THEREFORE, PROCESS AND UNIT DOSE

[75] Inventors: Yie W. Chien, North Brunswick, N.J.; Ajay K. Banga, Rochester, N.Y.

[73] Assignee: Rutgers, The State University of New Jersey, New Brunswick, N.J.

[21] Appl. No.: 587,406

[22] Filed: Sep. 25, 1990

[51] Int. Cl.⁵ .............................................. A61N 1/30
[52] U.S. Cl. ...................................... 604/20; 607/152; 607/153
[58] Field of Search ................. 604/20; 128/798, 802, 128/803

[56] References Cited
U.S. PATENT DOCUMENTS

| | | | |
|---|---|---|---|
| 4,383,529 | 5/1983 | Webster | 604/20 |
| 4,702,732 | 10/1987 | Powers et al. | 604/20 |
| 4,722,726 | 2/1988 | Sanderson et al. | 604/20 |
| 4,786,277 | 11/1988 | Powers et al. | 604/20 |
| 4,915,685 | 4/1990 | Petelenz et al. | 604/20 |
| 4,927,408 | 5/1990 | Haak et al. | 604/20 |
| 5,042,975 | 8/1991 | Chien et al. | 604/20 |
| 5,080,646 | 1/1992 | Theeuwes et al. | 604/20 |

*Primary Examiner*—Stephen C. Pellegrino
*Assistant Examiner*—Michael Rafa
*Attorney, Agent, or Firm*—Leroy G. Sinn

[57] ABSTRACT

Provided are reservoir electrodes for iontotherapeutic devices which have two chambers; the first chamber is electrically connected to the iontotherapeutic device and is designed to contain electrolytic solution and the second chamber has ionized pharmaceutical dissolved in electrolytic solution. The two chambers are separated by a permselective membrane. The first chamber has means to inhibit increase in ionic content caused by the operation of the iontotherapeutic device. Also provided are unit dose forms adapted for insertion into the reservoir electrodes. The dose unit forms are made of crosslinked polymer and contain ionizable pharmaceutical which is released for absorption during operation of the iontotherapeutic process. Also provided are novel iontotherapeutic devices and processes.

21 Claims, 13 Drawing Sheets

IONTOTHERAPEUTIC DEVICES, RESERVOIR ELECTRODE DEVICES THEREFORE, PROCESS AND UNIT DOSE

TECHNICAL FIELD

This invention relates to an iontotherapeutic device and reservoir electrodes therefore, for regulated transdermal systemic administration of ionizable pharmaceuticals (including ionizable biopharmaceuticals).

It also provides an iontotherapeutic process for transdermal administration of ionizable pharmaceuticals, particularly those which are otherwise transdermally absorbed to a small degree or not at all. The invention also relates to a unit dose in which an ionized pharmaceutical is dispersed. The unit dose is adapted to be assembled as a part of either the anode or the cathode, depending upon whether the ionized pharmaceutical is cationic or anionic, so that the ionized pharmaceutical will be delivered transdermally and then be absorbed systemically when the iontotherapeutic device is in operation.

BACKGROUND ART

Many pharmaceuticals are required to be administered by injection. Other pharmaceuticals may be administered orally, but in some cases, there is inefficient absorption into the bloodstream to permit the pharmaceuticals to achieve the intended therapy. Also, with regard to oral administration, many orally administered pharmaceuticals undergo a high degree of destruction by the hepato-gastrointestinal first-pass metabolism. Often the metabolites of the first-pass metabolism cause unwanted biological activity or toxicity. In oral administration, there are variables which cause undesirable variations in the extent of gastro-intestinal absorption from subject to subject, especially in the case of some pharmaceuticals; and there are also associated problems of uneven blood levels resulting from an initial large absorption with attendant undesirable side effects or toxicities, and subsequent blood levels which are less than therapeutically optimal.

There has been an increasing interest in transdermal delivery. However, transdermal absorption of a number of pharmaceuticals has not been satisfactorily developed for adequate therapy, since they have not been absorbed transdermally to any significant degree.

Investigations have been carried out to explore the delivery of certain therapeutic agents transdermally by use of iontotherapy. Development of previous reservoir electrode devices have been reported, for example, by Sanderson et al., U.S. Pat. No. 4,722,726 and references cited therein.

It is highly desired to provide new and improved iontotherapeutic devices, reservoir electrodes therefore, and devices, reservoir electrodes therefore, and iontotherapeutic processes and unit dose forms for use therein and to provide further thereby therapeutic levels of systemically-active pharmaceuticals efficiently with a physiologically-acceptable low electric current.

SUMMARY OF THE INVENTION

Provided by this invention is a pharmaceutical reservoir electrode for use in iontotherapeutic delivery of a pharmaceutical which is ionized and is contained therein, comprising:

a) a housing for said electrode;

b) a first chamber which contains an electrolytic solution to permit said iontotherapeutic delivery to take place and having present therein ion exchange resin in suitable form, which is capable of removing ions generated in the reservoir electrode in said first chamber as the iontotherapeutic delivery takes place;

c) an electrical connector to contact electrically the electrolytic solution contained in said first chamber and adapted to connect electrically with an iontotherapeutic device used for iontotherapeutic administration;

d) a second chamber for receiving said ionized pharmaceutical; and e) a permselective membrane separating said second chamber from said first chamber, said membrane characterized by having pores preferably with permeability sufficiently low to inhibit substantial passage of said ionized pharmaceutical present in said second chamber into said first chamber during said iontotherapeutic delivery of the ionized pharmaceutical.

The second chamber can preferably be open for receiving a unit dose adapted to be inserted into and to be secured in the open second chamber. Alternatively, the second chamber can be closed, i.e., having a wall or membrane covering the open mouth of the chamber to make it a closed chamber. In this event, the wall member or membrane member must be compatible with the ionized pharmaceutical to be administered iontotherapeutically and to be stable dimensionally. The outside wall member must also have the characteristic of permitting the pharmaceutical in ionized form to pass through in order to be administered during the iontotherapeutic process.

The closed second chamber in this alternative is provided with an opening into which the solution of the ionized pharmaceutical can be filled into the closed second chamber.

To be used in conjunction with the open second chamber, are provided herewith unit dose forms. These can be inserted into the open mouth of the second chamber. The inserted dosage unit rests in intimate contact with the permselective membrane, which separates the said second chamber from the said first chamber. The dosage unit can have an outside wall portion and a peelable membrane or wall portion covering the base surface of the dosage unit which will be removed before insertion of the dosage unit into the open mouth of the second chamber. Likewise, the outer surface of the dosage unit can be covered with a peelable wall portion or membrane. In this type of unit dose, the pharmaceutical is present in a hydrogel unit dose wherein the dissolved pharmaceutical in ionized form can be uniformly dispersed in a suitable and compatible hydrophilic polymer. The exterior surface of the unit dose can be any suitable material which permits an intimate contact with the skin of the subject being treated with the ionized pharmaceutical present in the unit dose. In making the unit dose wherein a suitable hydrophilic polymer is utilized, a selection is made of the hydrophilic polymer which is compatible with the ionized pharmaceutical present in the unit dose, as well as being sufficiently dimensionally stable to permit storage, transportation and utilization of the unit dose in the iontotherapeutic device employed in administering the ionized pharmaceutical. The solvent used to dissolve the pharmaceutical which has been dispersed in the dosage unit can be removed if desired by evaporation. In this embodiment, the unit dose can be wetted when preparing the unit dose for insertion into the second chamber with a suitable amount of sterile aqueous solution, such as an aqueous buffer having suitable ion content and pH.

The unit dose consists of a crosslinked polymeric material which is in hydrogel form. The unit dose is desirably formed by polymerizing a combination of a solution of the ionized pharmaceutical and the monomeric material used in forming the crosslinked polymeric hydrogeled unit dose. Polymeric material and the crosslinking agent, as well as any required catalyst composition, must be selected which is comatible with the pharmaceutical employed. The pharmaceutical must not react substantially with or be degraded by the components of the polymerization composition, and must be stable in the presence of the ingredients of the final crosslinked polymeric unit dose. The polymeric composition must provide a crosslinked polymer which is substantially free of components that are biologically unacceptable.

It has been found suitable to employ acrylamide along with a suitable crosslinking agent such as bis-acrylamide and catalyst composition, to provide a crosslinked polymeric hydrogeled dosage unit. It has been found acceptable to incorporate insulin as the ionized pharmaceutical to be incorporated into the crosslinked dosage unit adapted to be inserted in position within the open second chamber.

Also, it has been found desirable to incorporate along with insulin or other peptide pharmaceutical an agent which will inhibit or prevent proteolytic degradation after the ionized pharmaceutical has been transdermally absorbed in the iontotherapeutic process. One suitable agent to inhibit such proteolytic degradation has been found to be a protease degradation inhibitor, such as aprotinin. Other peptide pharmaceuticals which are ionizable can be also used in conjunction with a suitable proteolytic degradation inhibitor, either a protease inhibitor or another effective inhibitor of proteolytic degradation, which is compatible with the dosage unit and biologically compatible with the pharmaceutical component as well as the skin and body of the subject being treated.

The ionized pharmaceutical solution can be contained in a unit dose form such as a disposable polymeric unit dose form to which a dosage amount of an ionized pharmaceutical solution (pH desirably at least about 1.0, 1.5 or about 2 pH units above or below the pKa or isoelectric pH of the ionized pharmaceutical if the pharmaceutical is peptide in nature) is dispersed in a polymer which is characterized by being compatible with the pharmaceutical as well as the skin, hydrophilic, and capable of releasing the pharmaceutical for iontotherapeutic transdermal absorption.

The unit dose form used with the reservoir electrode of the invention can also comprise a sterile solution of the ionized pharmaceutical contained within a closed reservoir unit dose form having a drug-releasing microporous membrane surface. The unit dose forms are prepared to provide the ionized pharmaceutical to be delivered iontophoretically through the skin of the subject treated and to provide iontotherapeutic transdermal absorption of a systemically effective amount of the pharmaceutical.

The unit dose forms are maintained covered to retain sterility until the desired time of iontotherapeutic administration. Alternatively, the unit dose forms can be sealed under sterile conditions in individual pouches.

The pharmaceutical reservoir electrode which will receive such a unit dose form is used as a part of a suitable iontotherapeutic device, which can be used to carry out the iontotherapeutic delivery and transdermal absorption of the ionized pharmaceutical. The pharmaceutical reservoir electrode is either a cathode or an anode depending upon whether the pharmaceutical is in anionic or cationic form, respectively. The iontotherapeutic device desirably provides, in the process, an iontotherapeutically effective and physiologically acceptable periodic pulse current with a specific waveform having an amplitude up to about 10 mA based on a reservoir electrode skin-contacting area of about 5 $cm^2$ and an effective frequency of at least about 10 Hz up to about 50 KHz until the subject treated has received a pharmacologically-effective systemic dosage of the ionized pharmaceutical.

The pharmaceutical in the dosage unit can be selected from pharmaceuticals which can be ionized, including those which ordinarily are not transdermally absorbed through intact skin in an effective dosage amount, such pharmaceuticals including but not limited to insulins, vasopressin, heparin, growth hormones, glucagon, oxytocin, calcitonin and other macromolecular drugs as well as a number of others which can be provided in ionized form. A number of compounds which are naturally-occurring in humans, and which often are peptide in nature, are also included within this pharmaceutical group, many of which can be produced identically or as a related compound using DNA recombinant or other biological techniques.

DETAILED DESCRIPTION OF THE INVENTION AND THE PREFERRED EMBODIMENTS

Figure 1:
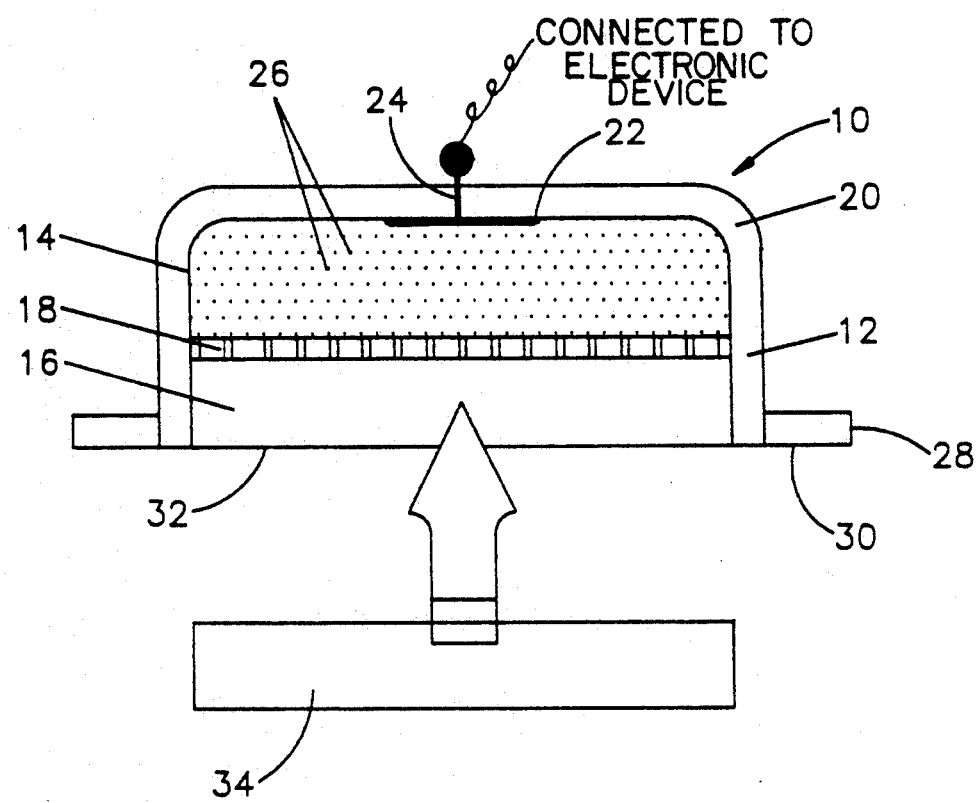
FIG. 1 is a cross section of a reservoir electrode device of the invention having first and second chambers, the open mouthed second chamber shown receiving a hydrogel dose unit having a peptide drug dispersed therein.

FIG. 1 is a cross section of reservoir electrode 10 of the invention. The electrode has a housing 12, which can be made of a polymeric material or other suitable material which is non-conductive and dimensionally stable. Suitable polymeric material can be selected from high density polyethylene, polypropylene, polyoxymethylene, polycarbonate or the like. The housing 12 can be molded following conventional molding procedures. The housing is shaped so to form a cavity comprising the first chamber 14 and second chamber 16. The first chamber 14 and the second chamber 16 are separated by membrane 18. Membrane 18 is a permselective membrane which has pores which are preferably sufficiently small to inhibit the pharmaceutical molecules present in the second chamber 16 from substantial migration into first chamber 14 but are sufficiently large to permit full aqueous contact of the electrolytic solutions contained in the first and second chambers. A suitable permselective membrane is selected depending upon the pharmaceutical being iontotherapeutically administered, and the pH selected for the electrolytic solutions contained in the first and second chambers. Illustrative permselective membranes are commercially available as Nucleopore membranes, Millipore membranes, Spectra/por membranes and others. The permselective membrane is placed into housing 12 in intimate contact with the gel polymeric unit 20 contained in the first chamber 14. The permselective membrane is maintained in place by friction fit against the inside wall of housing 12, by adhesive to the housing 12, or by snap fit into a receptive groove which can be formed nto the inner wall of housing 12, or the like means to maintain the permselective membrane in place.

A hole is centrally disposed in the base of housing 12 to permit passage of electrical conduit 24, which is attached electrically to electrical contact 22. Electrical contact 22 can be formed of any suitable electrically conductive material to make intimate electrical contact with the gel unit 20. Electrical contact 22 can be suitably shaped from a metallic foil, e.g., from platinum foil. Gel unit 20 has dispersed therein suitable anionic or cationic resin particles 26. The resin particles are dispersed in the polymeric hydrogel unit dose 20 in a manner to inhibit an increase in the ionic content of the electrolytic solution of first chamber 20 during operation of the iontotherapeutic process wherein electrode 10 is an assembled element of the iontotherapeutic device used in carrying out the process. more full description of the preparation of gel unit 20 follows herein. The housing terminates with a flange 28, which extends outwardly in a direction perpendicular to the vertical wall of the housing. On the outer surface of flange 28, is present an adhesive layer 30, which adheres to the skin of the subject during iontotherapeutic treatment. Suitably, the adhesive layer 30 is protected during storage and shipment until the electrode is being readied for iontotherapeutic use by application thereto of a peelable film which is biologically acceptable and adheres until it is desired to remove by peeling. Shown also is unit dose 34, which is formed of a polymeric hydrogel. It is shaped into such dimension that it can be pressed into second chamber 16 to fill it and remain secured in place. The upper surface of dose unit 34 will be brought into intimate electrical contact with permselective membrane 18. The preparation of dose unit 34 will be described in greater detail hereinafter.

In illustration, a unit dose can be made using polyacrylamide as a hydrophilic polymer and insulin as the pharmaceutical. The pharmaceutical insulin is dissolved in an acrylamide buffer solution. A suitable aqueous buffer for use is a citrate buffer having a pH at least 1 and preferably at least 2 pH units below the isoelectric pH of insulin (pH 5.3—isoelectric point of natural commercial insulin). A suitable ionic strength is also used. A suitable buffer has been found to be a pH 3.6 citrate buffer, ionic strength 0.1M. It is convenient to use a buffer of higher ionic strength to permit dilution through addition of the pharmaceutical solution and other additions to enable a final desired ionic strength. Using a buffer of double the final desired strength has been found suitable.

To 100 parts by weight of the double strength buffer, 15 parts by weight of acrylamide can be added and stirred to dissolve the acrylamide, which provides a 7 percent by weight of acrylamide. To this is added a suitable crosslinking agent. For this purpose, bis-acrylamide has been used. An amount of 1.05 parts of the total volume of acrylamide buffer solution is added. To this solution, it has been found suitable to add a preservative agent. It has been found suitable to add gentamycin sulfate at about 50 micrograms/ml of the solution and 50 micrograms of bacitracin per ml of the solution. Also, it has been found desirable to add urea to the solution in a suitable amount, for example at a concentration of about 2 mg/ml solution (or other suitable agent) to minimize adsorption of the pharmaceutical to the polymer used to make the unit dose and further to inhibit the aggregation of the insulin molecules to form fibrils. The solution is stirred to form a uniform solution.

A catalyst system of ascorbic acid (0.1 percent, w/v), ferrous sulfate (0.0025 percent, w/v) and hydrogen peroxide (0.03 percent of 30 percent stock, w/v) has been found suitable to polymerize acrylamide in forming the unit dose.

The ascorbic acid and ferrous sulfate catalyst components are added to the acrylamide solution with stirring. Then, the insulin solution component is added to the acrylamide solution in a suitable concentration, a 100 IU/ml (3.8 mg/ml) concentration has been found suitable.

Amounts of the insulin-acrylamide solution are added to suitable molds of the shape of the second chamber of the reservoir electrode. Molds made of polyethylene tetrafluoride, sold under the designation Teflon, have been found suitable for use in making unit doses and a suitable amount of the solution to form an individual unit dose has been found to be 150 microliters. A greater or lesser amount can be used depending upon the volume of the second chamber of the electrode and other factors. Then, a suitable polymerizing amount of hydrogen peroxide (or other suitable initiator), is added to initiate polymerization. A 10-15 microliter dilution has been found suitable. The acrylamide-insulin solution is stirred gently for a brief period. In a short time, such as about one-half minute, polymerization occurs to provide a dose unit consisting of a transparent hydrogel unit dose containing insulin uniformly distributed. Sodium bisulfite can be used to remove, if desired, any remaining traces of acrylamide, as is known.

The insulin-containing unit dose can be evaluated for transdermal absorption property for iontotherapeutic administration using the Valia-Chien cell and procedure.

The above procedure in the alternative can be repeated using another polymer as the hydrogeled material. Again, monomeric material is employed and is polymerized in the presence of the ionized pharmaceutical, such as insulin, in illustration. The final polymeric hydrogel material is poly-2-hydroxyethylmethacrylate (referred to as p-HEMA). The p-HEMA polymer hydrogel can be prepared in crosslinked form by utilizing the following illustrative composition: HEMA, 40%; ethylene glycol dimethacrylate (referred to as EGDMA), 0.8%; suitable catalyst, such as the azonitrile catalyst, 2,2'-azo-bis-isobutyl nitrile (referred to as AIBN), 0.02%; water, 35%; glycerin, 25%. All the ingredients of this composition are mixed together. AIBN and EGDMA can be added in appropriate small quantities from concentrated stock solutions dissolved in ethanol. A mixture of HEMA, a crosslinker, initiator, water and a plasticizer (glycerin) can then be purged with nitrogen for a period of time to remove oxygen, for example, 5-30 minutes.

The polymerization mixture can then be added to a suitable molds, such as polytetrafluoroethylene molds. The molds are covered suitably by use of polytetrafluoride films. Polymerization is then carried out at an elevated temperature suitable for the polymerization, such as 90° C. for an appropriate time. It has been found suitable to employ about one hour.

Upon polymerization, the final transparent hydrogel discs are removed from the molds and are extracted thoroughly with distilled water to remove residual polymerization mixture or components such as the HEMA monomer. It has been found that continuous extraction with distilled water for a 48-hour period is ordinarily sufficient. The dose forms provided are dried.

Upon completion of the extraction, insulin solution using pH 3.6 citric buffer can be used to saturate the dried hydrogel unit forms. The insulin solution used can suitably be 0.65 mM. The concentrated citric buffer is added as referred to above, i.e., 0.1 mM. Therefore, after a period of saturating the hydrogel disc, the insulin discs are removed from the insulin solution and are wiped to remove residual solution remaining on the surface of the unit doses. They are then placed back into the molds.

In summary, suitable momomeric materials can be employed along with suitable crosslinking agents to provide the crosslinked dosage unit containing in the final unit dose form a unit dose amount of a selected ionized pharmaceutical wherein the crosslinked polymer hydrogel is biocompatible, compatible with the ionized pharmaceutical and capable of releasing the ionized pharmaceutical to be administered in the iontotherapeutic process. Sufficient crosslinking of the hydrogel polymer should be provided to result in dimensionally stable dosage units. The final dosage unit should be free of unwanted polymerization composition residues such as residual monomer and catalytic components.

Also, if desired, certain pre-polymerized non-crosslinked polymers can be employed to intermix with an aqueous solution of a selected ionized pharmaceutical, which is appropriately buffered or adjusted in pH, for example, at least one or two pH units below the pka or the isoelectric point of the pharmaceutical if the pharmaceutical is peptide in nature. The polymer and aqueous buffer solution of the ionized pharmaceutical can then be crosslinked using a suit able crosslinking agent for the polymer which has appropriate crosslinking sites such as points of unsaturation. In making the selection of such polymers and such crosslinking agents, it must be born in mind the stability of the pharmaceutical in such final unit doses after the crosslinking and the adequacy of the release factor of the pharmaceutical to assure desired iontotherapeutic absorption is achieved.

As expressed above, suitable proteolytic degradation inhibitors or combinations thereof can be added to the insulin solution or other peptide solutions used in the dose unit preparation to inhibit proteolytic degradation upon the absorption of the pharmaceutical into the skin. For example, aprotinin, a proteolytic degradation inhibitor, can be added to the insulin solution (or peptide pharmaceutical solution) used in the unit dose preparation. It has been found that about 0.1 to about 0.2 mM concentration of the proteolytic degradation inhibitor is suitable, desirably a 0.15 mM concentration is used. It is desirable to employ a pH in the dose unit substantially below or above the isoelectric pH of the proteolytic degradation inhibitor employed.

Preparation of other unit doses can be carried out by selecting other ionizable pharmaceuticals including other peptide pharmaceuticals such as vasopressin, growth hormone, calcitonin and the like.

Figure 3:
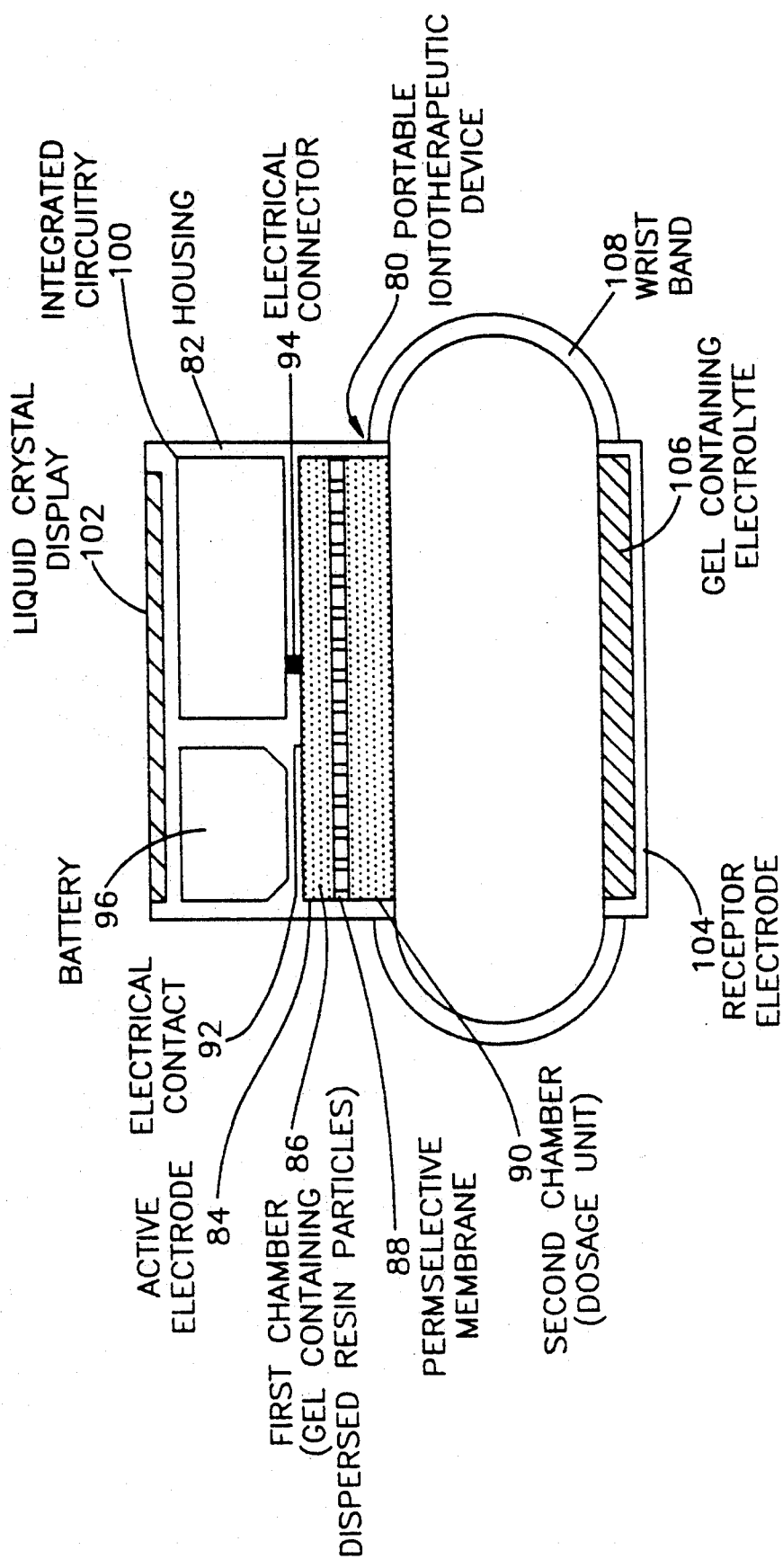
FIG. 3 is a partial cross section of another embodiment of a portable iontotherapeutic device of the invention showing a battery power source, liquid crystal display, integrated circuitry, a reservoir electrode of the invention, an installed dosage unit of the invention, a wrist band for attachment of the iontotherapeutic device to the wrist of the subject treated, said wrist band having a receptor electrode in the wrist band opposite the installed unit dose.
Figure 4A:
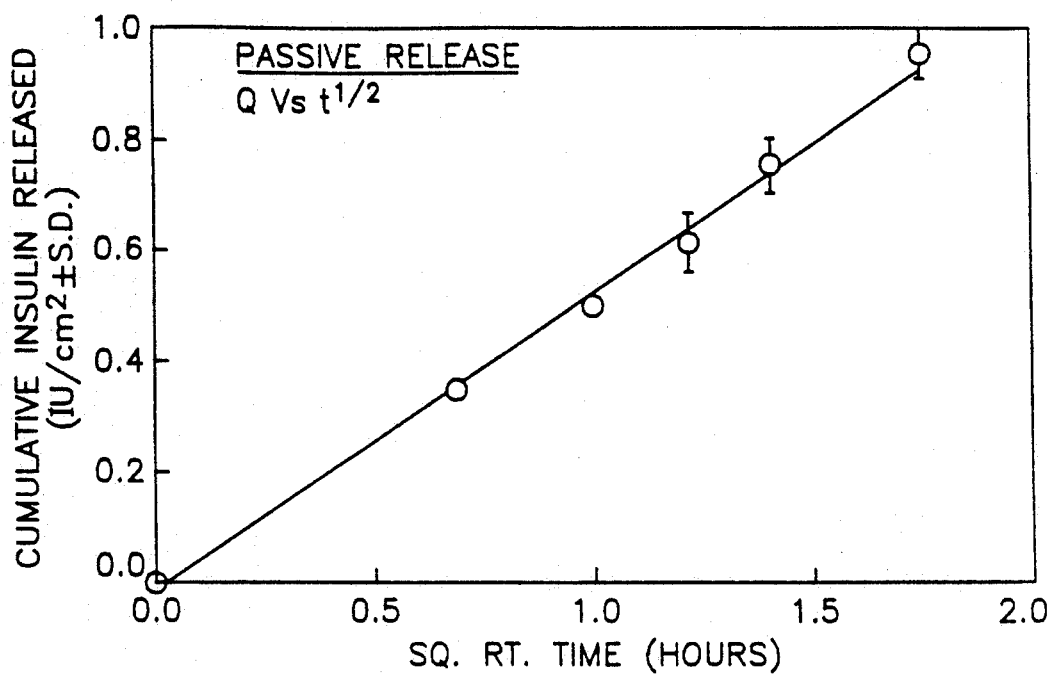
FIG. 4A is a graph showing passive release of insulin from a polyacrylamide dose unit follows Q Vs. $t^{\frac{1}{2}}$ relationship.
Figure 4B:
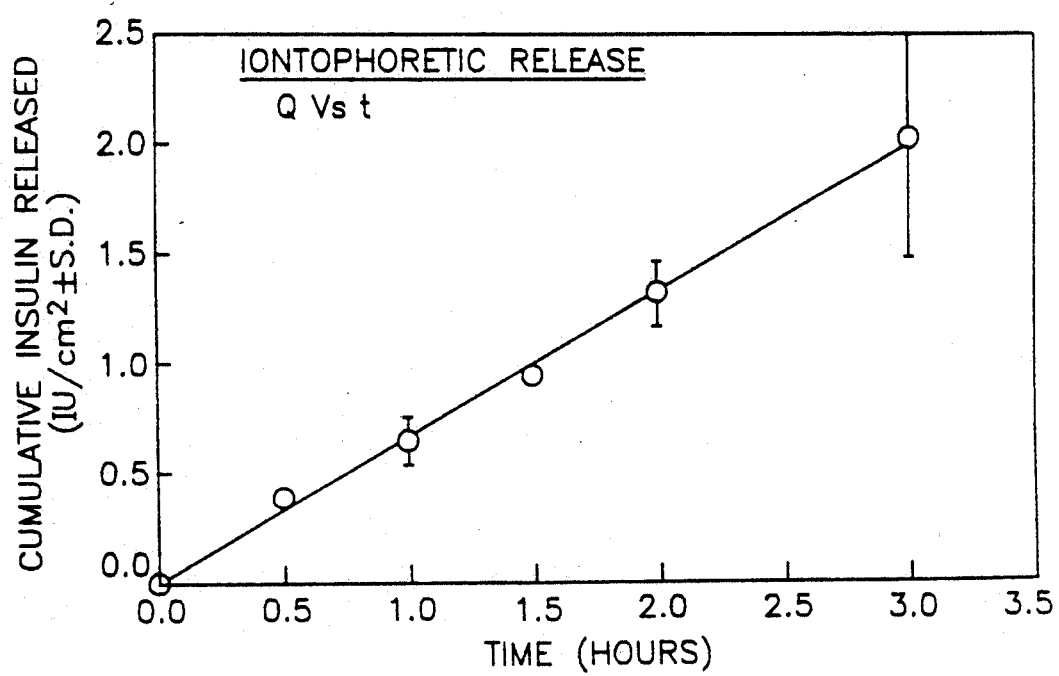
FIG. 4B is a graph showing that an iontotherapeutic release follows Q Vs. t relationship.
Figure 5:
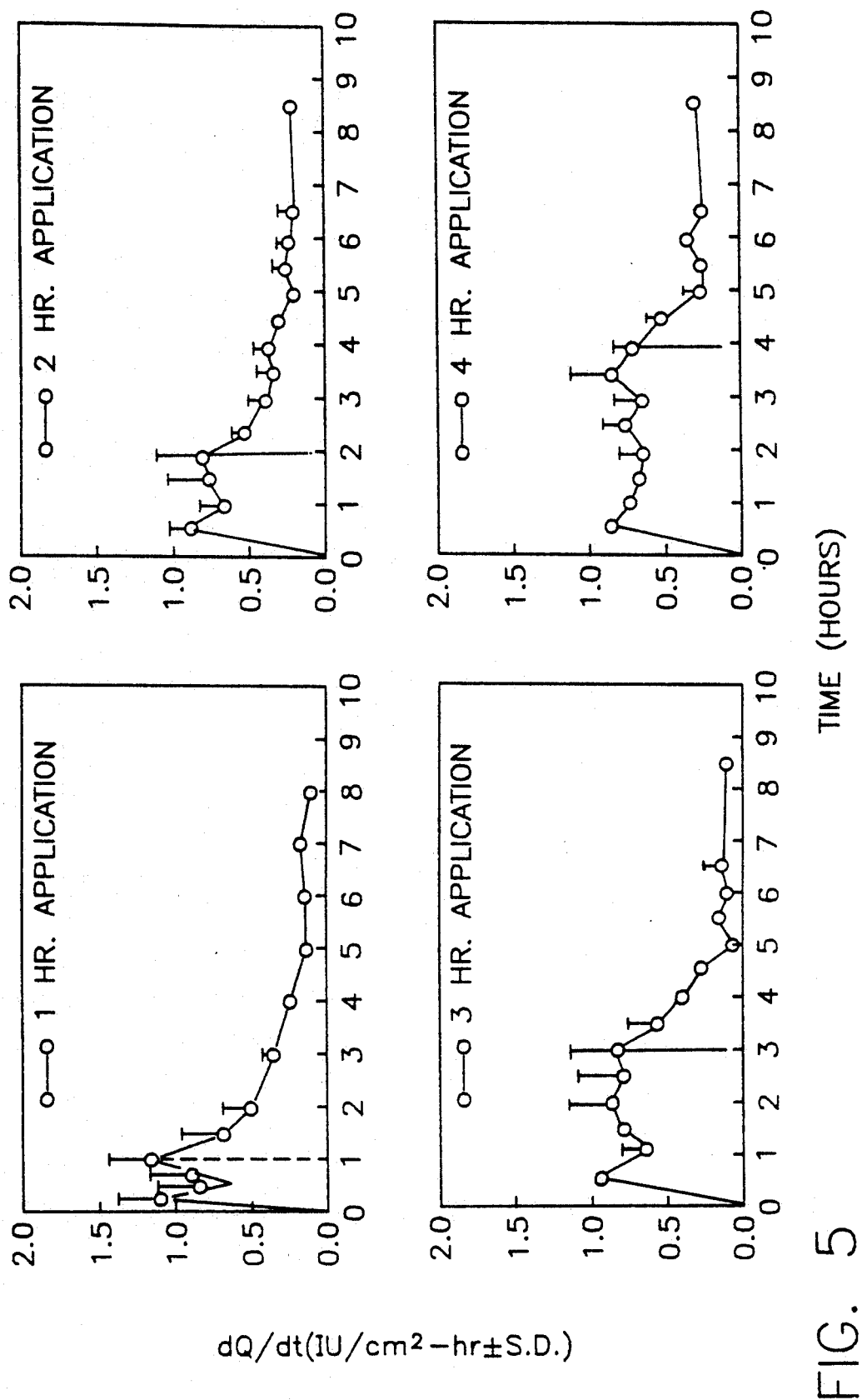
FIG. 5 shows four graphs in which current has been applied in iontotherapeutic administration of insulin for increasing time periods - 1, 2, 3 and 4 hours, respectively. The increasing release rate (dQ/dt) of insulin from a polyacrylamide hydrogel dosage unit is shown to prolong with the increase in the duration of current application.
Figure 6:
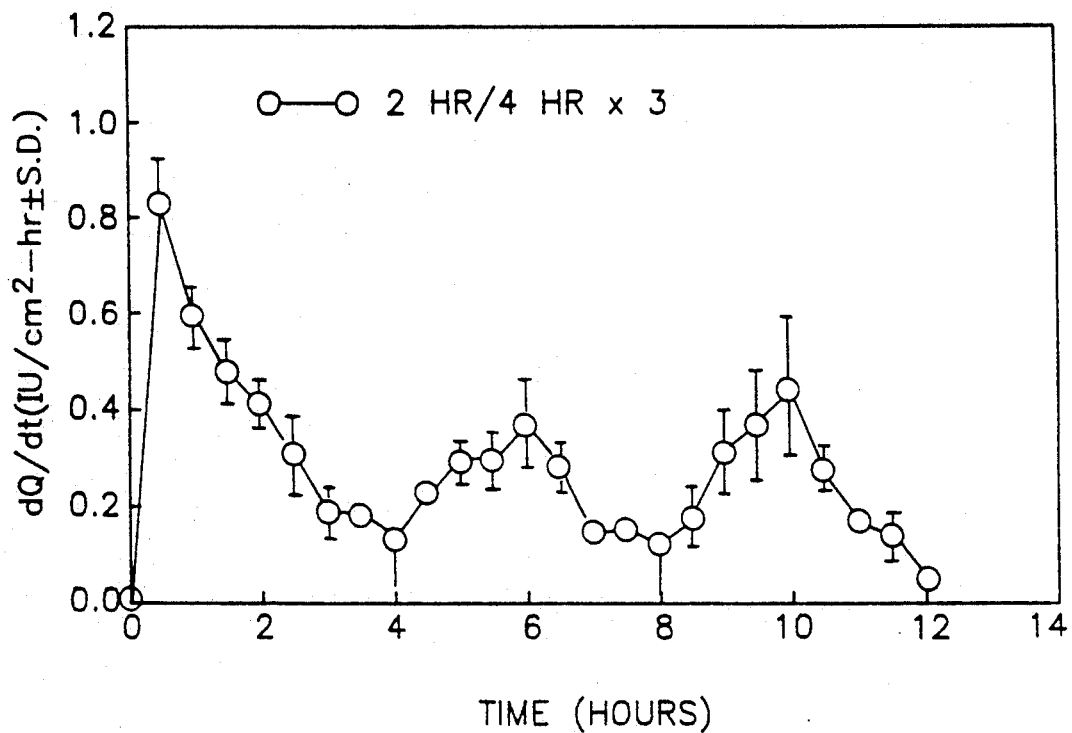
FIG. 6 is a graph showing modulation of the release rate (dQ/dt) of insulin from polyacrylamide hydrogeled dosage unit by multiple applications of current.
Figure 7A:
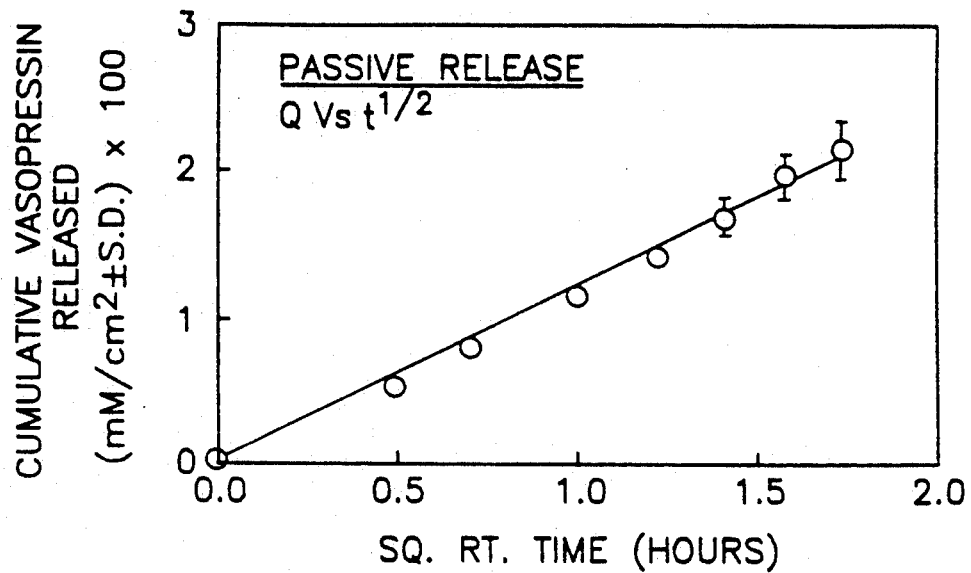
FIG. 7A is a graph showing passive release of vasopressin from a polyacrylamide hydrogel dose unit to follow Q Vs. $t^{\frac{1}{2}}$ relationship.
Figure 7B:
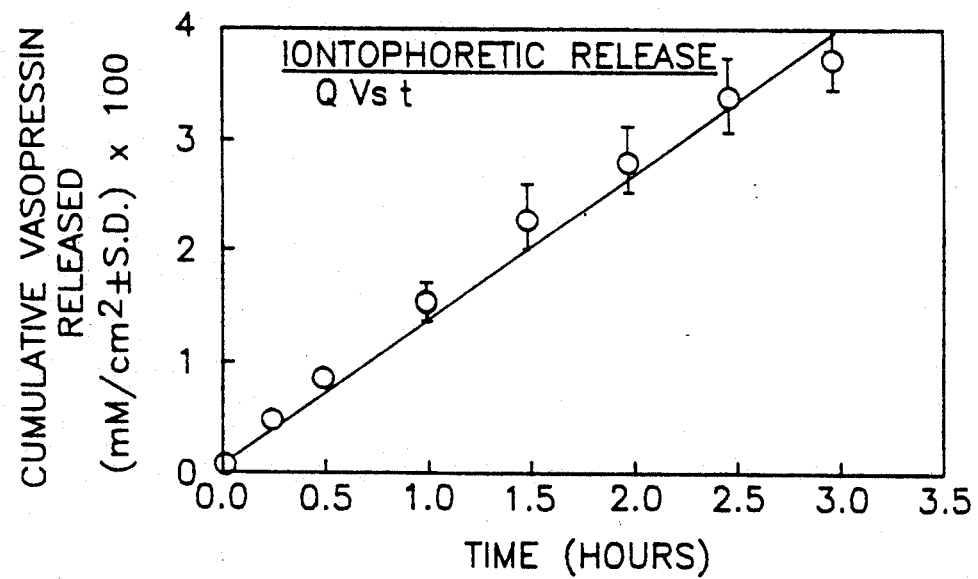
FIG. 7B is a graph showing corresponding iontotherapeutic release to follow Q Vs. t relationship.
Figure 8:
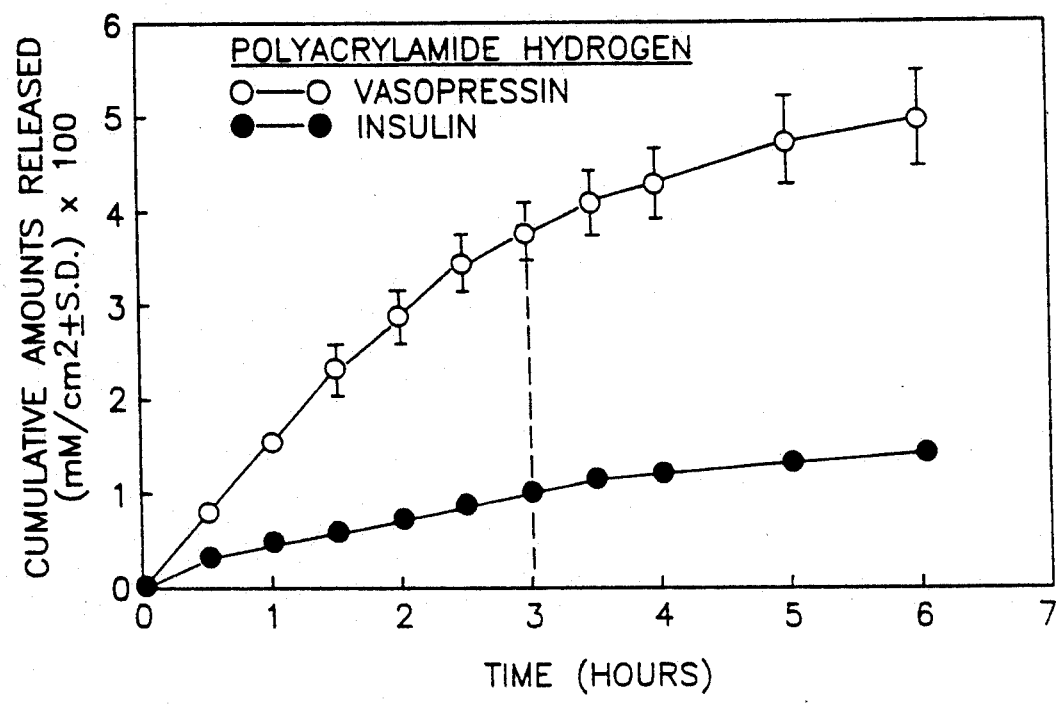
FIG. 8 is a graph showing iontotherapeutic release profiles of vasopressin and insulin from polyacrylamide hydrogel dosage units for 3-hour current application periods.
Figure 9:
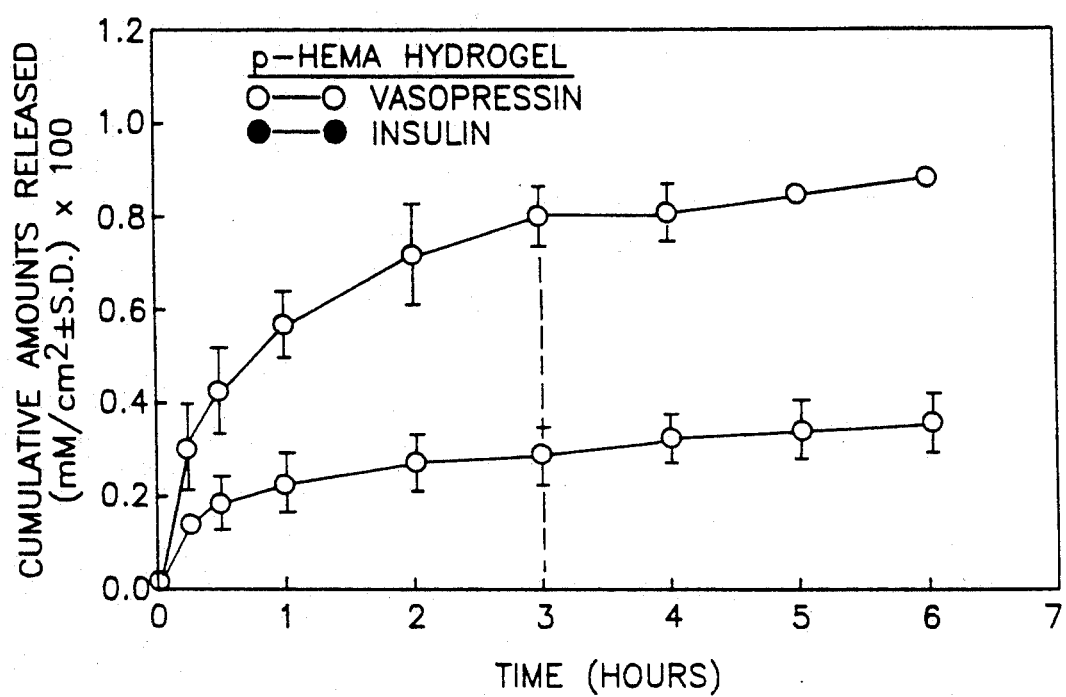
FIG. 9 is a graph showing iontotherapeutic release profiles of vasopressin and insulin from p-HEMA hydrogel dose units for a 3 hour current application period.
Figure 10:
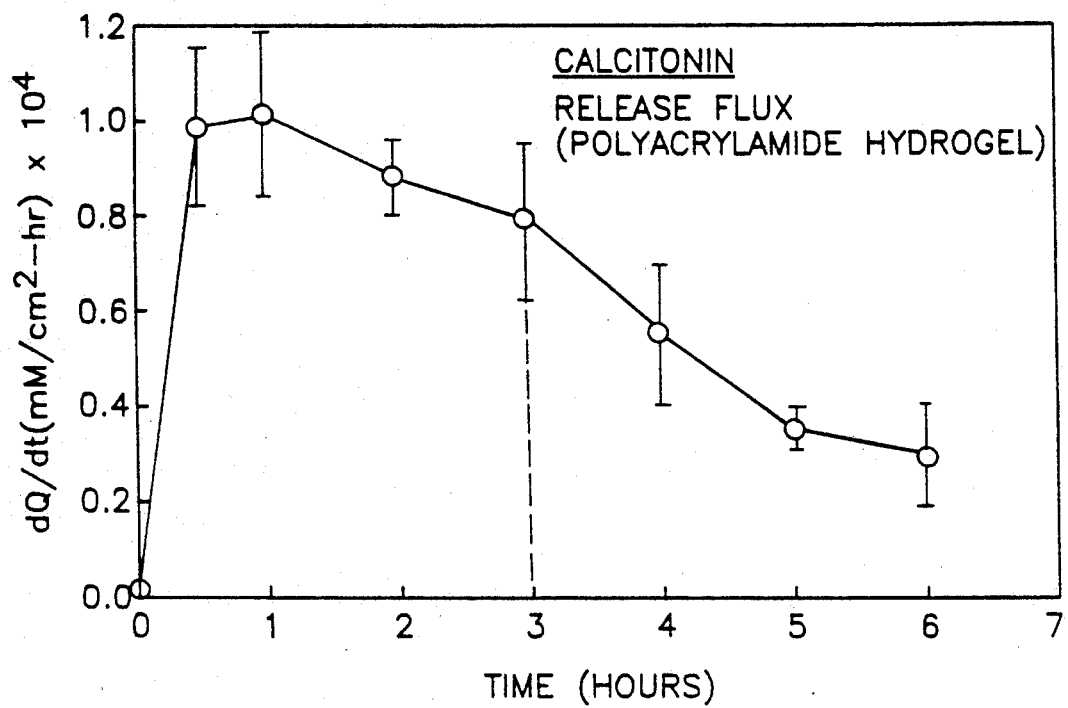
FIG. 10 is a graph showing iontotherapeutic release rates (dQ/dt) of calcitonin from polyacrylamide hydrogel dose unit for a 3-hour current application period.
Figure 11:
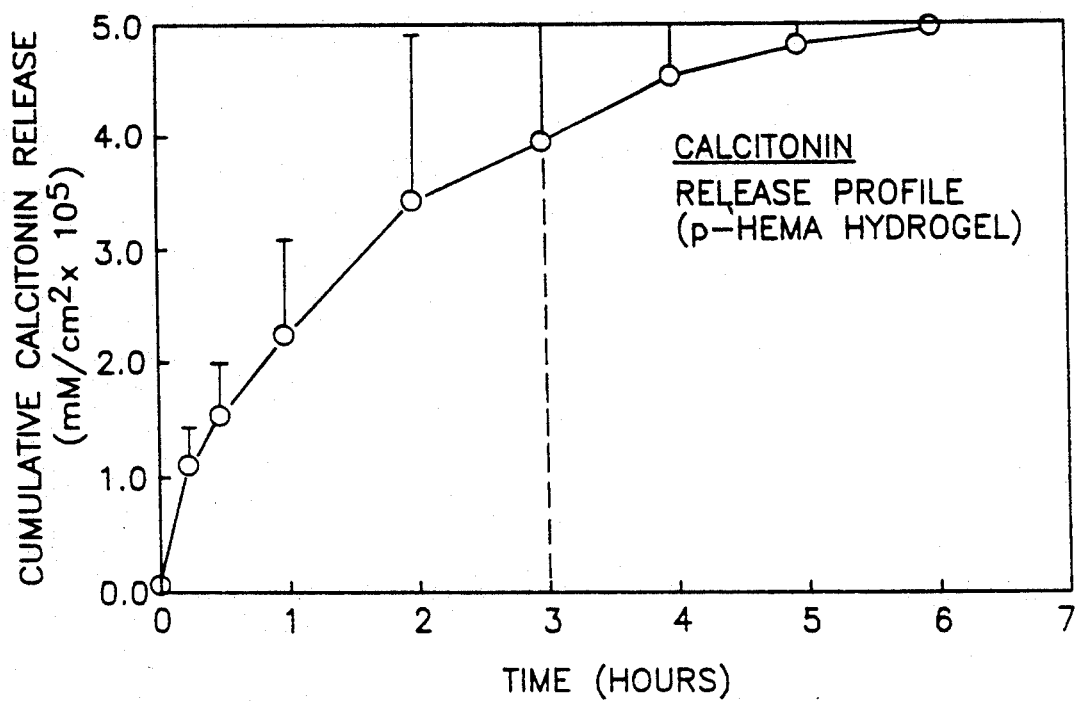
FIG. 11 is a graph showing iontotherapeutic release profile of calcitonin from p-HEMA hydrogel dose unit for a 3-hour current application.
Figure 12A:
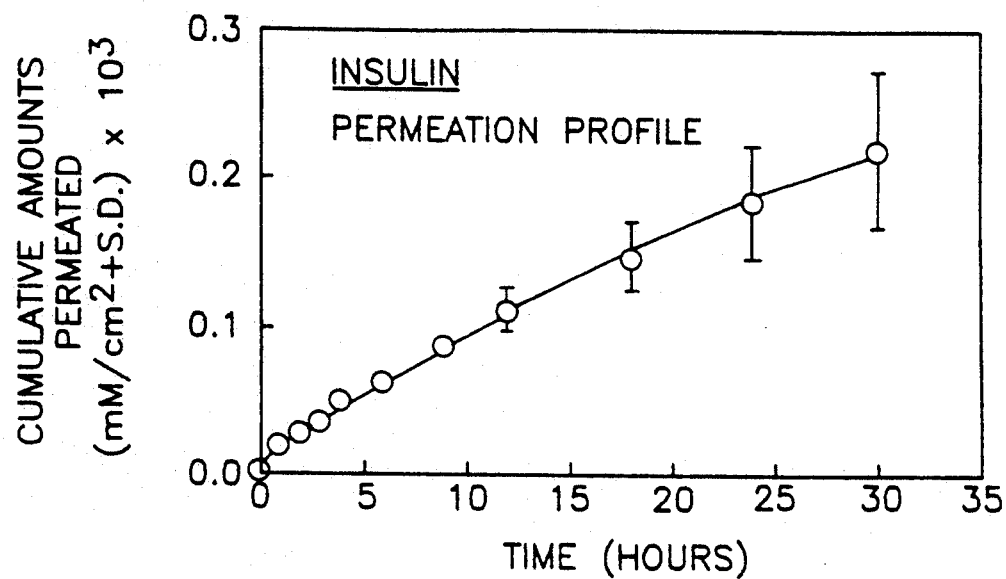
FIG. 12A is a graph showing iontotherapeutic permeation profile of insulin from polyacrylamide hydrogel dose unit across hairless rat skin for a 3-hour current application.
Figure 12B:
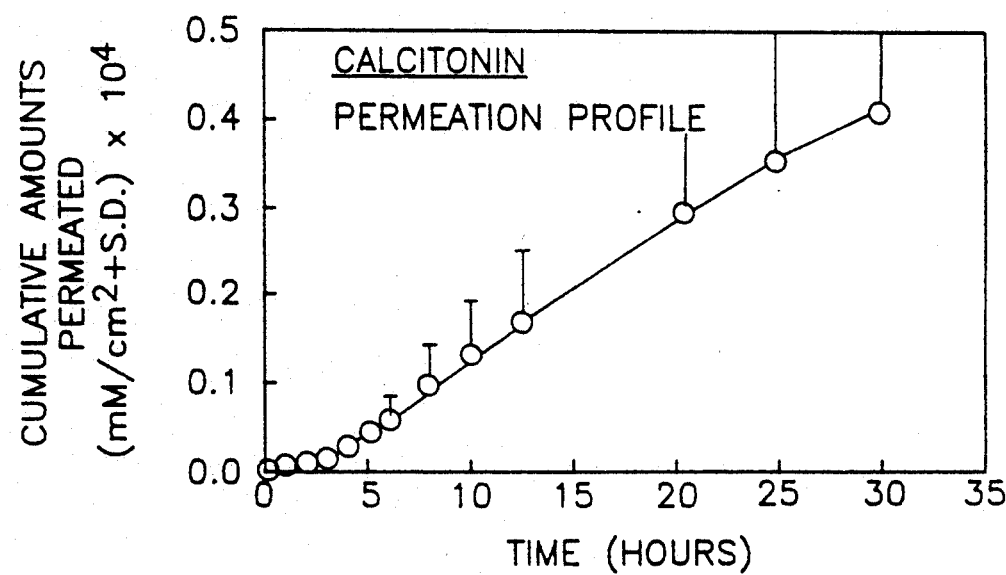
FIG. 12B is a graph showing iontotherapeutic permeation profile of calcitonin from polyacrylamide hydrogel dose unit across hairless rat sin for a 3-hour current application.
Figure 13:
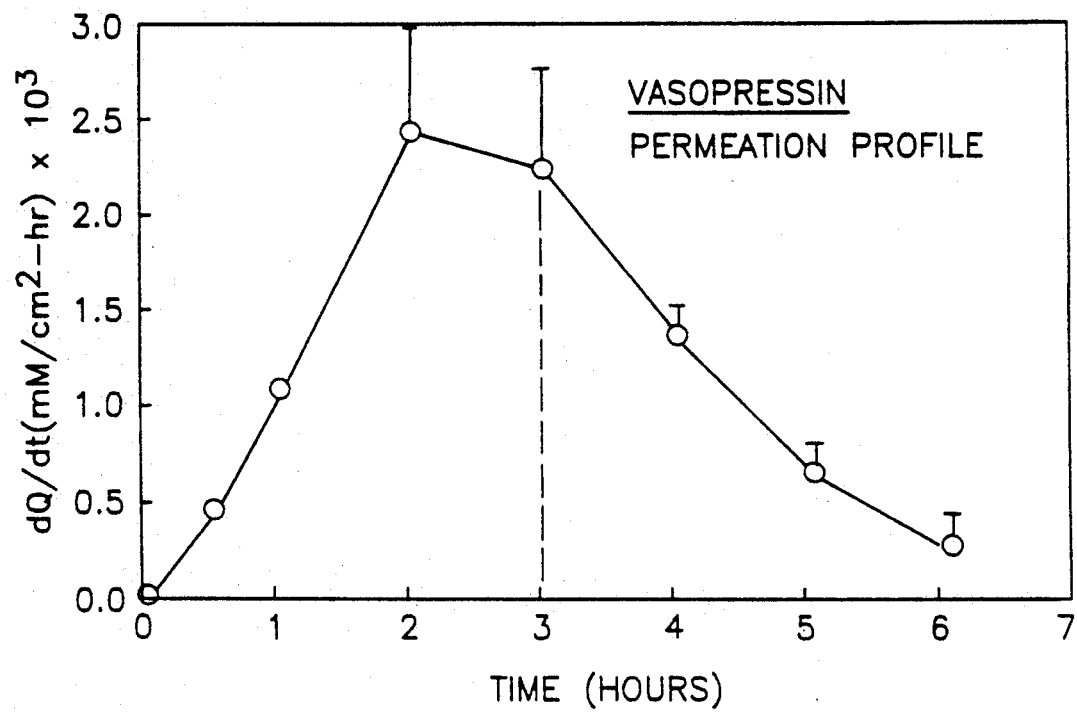
FIG. 13 is a graph showing iontotherapeutic permeation rate (dQ/dt) of vasopressin from polyacrylamide hydrogel dose unit across hairless rat skin for a 3-hour current application.

In carrying out the iontotherapeutic process using the unit doses and the reservoir electrode devices provided herein, an iontotherapeutic device for the administration is employed. An iontotherapeutic device as illustrated in FIG. 3 can be employed in this administration.

In carrying out the iontotherapeutic process of this invention, a dosage unit as provided herein is utilized with a reservoir electrode as provided herein. The electrode therapeutic device utilized is shown in illustration by FIG. 3. In FIG. 3, the power source 96 can be a suitable button type battery, such as a 6-volt battery. The integrated circuitry 100 utilized can be selected from known circuits for iontotherapeutic devices. It is desirable to utilize circuits as shown in International Patent Publication WO-88/00846, published Feb. 11, 1988, which is incorporated herein by reference. It is preferred to utilize integrated circuitry which provides periodic DC current in the iontotherapeutic administration. It is preferred to utilize pulse current in the administration of up to about 10 mA based on a reservoir electrode/skin-contacting area of about 5 $cm^2$. Current density is suitably in the range of about 0.1 to about 1 $mA/cm^2$, desirably about 0.5 to about 0.8 $mA/cm^2$, with about 0.6 $mA/cm^2$ having been found satisfactory. In the administration, it is preferred to use a periodic waveform in the square, triangular, sinusoidal, trapezoidal, or other acceptable geometric forms, or combinations thereof.

Further, the circuitry desirably provides an on/off ratio of from 1/50 to 10/1. Additionally, it is desired to utilize a physiologically acceptable repetition frequency of at least about 10 Hz up to about 50 KHz, or more if physiologically acceptable.

Some pharmaceuticals, especially certain relatively low molecular weight pharmaceuticals, can be iontotherapeutically administered using periodic DC mode or periodic wave mode. For example, the periodic DC mode can be "on" for about 0.5 to about 60 minutes, preferably about 1 to about 30 minutes per hour. During the intervening period during the hour, the device is in "off" position. The "on" can be more frequent or less frequent as desired to provide effective treatment. In the dosage currents, the on/off ratios in the dosage units and the devices described herein can be used or adapted to be used in the practice of the iontotherapeutic process of this invention.

A few hours duration of treatment each day following either procedure is ordinarily adequate, for example, two to ten hours, depending upon factors such as the pharmaceutical, the subject being treated, the iontotherapeutic factors selected and the like.

With regard to the making of the unit dose, there are a number of polymers which can be used to make the polymeric unit dose. In general, the polymer must be essentially nonionic, hydrophilic and compatible with the ionized pharmaceutical and the skin. The polymer used in making the dosage unit must permit the ionized pharmaceutical to be released during the operation of the iontotherapeutic device. The final polymers which are suitable in making the dosage unit are usually referred to as being in the category of hydrophilic polymers or hydrogels. These are preferably as pointed out above, selected from those that can be polymerized in situ. Also polymers which can be utilized can be selected from those which are pre-polymerized and have certain cross-linkable sites such as vinyl groups, hydroxy groups, carboxyl groups, amine groups, or other suitable groups which are suitable for crosslinking in making the unit doses of the invention. The particular polymer utilized is mixed with an aqueous solution of a pharmaceutical in which the pH of the solution is suitably adjusted to be substantially above or below the pKa or the isoelectric point if the pharmaceutical is peptide in nature.

With respect to the electrolytic solution present in the first chamber, it can suitably be in the form of a preformed electrolytic solution disc wherein suitable ionic exchange resin granules are suspended in the electrolytic solution having a suitable pH. The electrolytic solution discs can be formed, generally speaking, following the procedure described above for making unit dose forms. A monomeric material, crosslinking agent, aqueous buffer, catalyst composition, stabilizers, preservatives and other desired ingredients are added together with stirring. A desired amount of suitable resin granules are added and stirring or agitation is carried out adequately to get a thorough distribution of the selected ion exchange resin granules. Polymerization can be done as illustrated above with respect to the dose unit. The exact polymerization procedure and other procedures utilized in making this electrolytic disc unit for utilizing in the first chamber can be selected in accordance with the configuration of the cavity of the first chamber. As in the case of the dosage unit, the electrolytic disc is sufficiently polymerized and crosslinked to be dimensionally stable to hold the ion exchange resin granules utilized in uniform distribution.

The ion exchange resin granules are selected from cationic or anionic exchange resins. Cationic exchange resins have ion active groups with which cations react or are bound. The functional groups are normally acidic, for example are sulfonic, carboxylic or phenolic groups. Alternatively, the ion exchange resin can be anionic exchange resins which have ion active groups with which anions react or are bound. The anionic exchange can have in illustration a polyamine structure. Ion exchange resin used are water insoluble.

The particle size of the ion exchange resin can vary depending upon the ion exchange selected, the amount used, and other factors. It has been found that generally a particle size in the range of from 100 to about 200 micrometers, suitably about 150 micrometers. Suitable ion exchange resins of both anionic and cationic exchange types are available commercially for use in carrying out the invention.

Permselective membranes suitable for use in carrying out the invention are available commercially, as noted above. A permselective membrane will ordinarily be selected having pores with sufficiently low permeability with regard to the ionized pharmaceutical used to prevent substantial passage of the ionized pharmaceutical molecules into the first chamber. The permselective membranes are usually made of selected polymeric materials. The membranes will be selected which are compatible with the ionized pharmaceutical used in the iontotherapeutic administration, are stable structurally in its use in separating the first and second chambers and do not substantially interfere with the functioning of the desired iontotherapeutic process using the reservoir electrode having such permselective membrane.

Alternatively, the ion exchange resin granules present in the first chamber can be present in the form of a coating to a pre-formed polymeric lattice which has a shape to fit into the configuration of the first chamber. The lattice can be a series of concentric circles held in spaced relationship by cross members, can be in a form of an open celled matrix such as a honeycomb shape, or a type of ladder lattice form. Alternatively, the resin granules can be affixed to the bottom wall of the first chamber and/or to the sidewall portion of the first chamber. This can be accomplished by affixing to the bottom wall or the side wall or both a suitable resin film having suitable anionic or cationic resin as the need requires. Such resin films can be affixed as by following conventional procedures, for example, as by using heat sealing, a suitable adhesive or like procedures. In the event that resin film is applied to the side wall or the bottom wall or a lattice is used as described above or combinations thereof, the electrolytic solution can be present in the first chamber as a flowable solution, rather than being held in the crosslinked electrolytic polymeric disc. Also there can be utilized in making the first chamber to provide its capability of withdrawing ions generated during the iontotherapeutic process, a second membrane which can be placed contiguously to the permselective membrane 18 as shown in FIG. 1. Such resin film layer can be held in place by usual or customary means such as by clamping or adhesion on the periphery of the permselective membrane and the resin film layer. Again, combinations of such resin film layer and coatings on the bottom wall or side wall or the resin coated lattice or with the electrolytic unit disc having uniformly suspended therein resin granules.

When granules are utilized, they will be selected depending upon the amount of resin that is used, the amount of ions generated during the iontotherapeutic process utilized, the pharmaceutical utilized and the length of iontotherapeutic administration and other factors. It will be apparent to those skilled in the art by the description herein what the operative amount will be in a specific iontotherapeutic process carried out according to this invention.

Figure 2A:
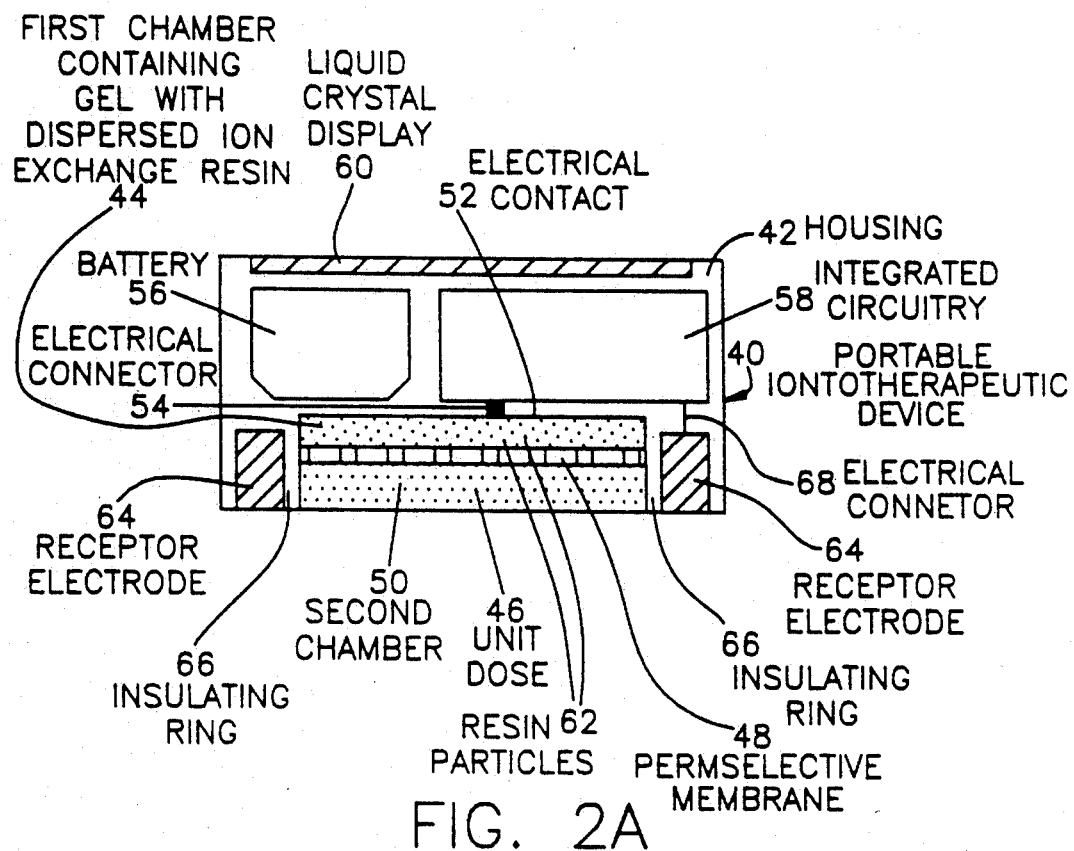
FIG. 2A is a cross section of a portable iontotherapeutic device which can be attached to a subject being treated iontotherapeutically, said device having integrated therein a reservoir electrode device of the type shown in FIG. 1 and a dosage unit of the invention being in operating position in the second chamber of the reservoir electrode.
Figure 2B:
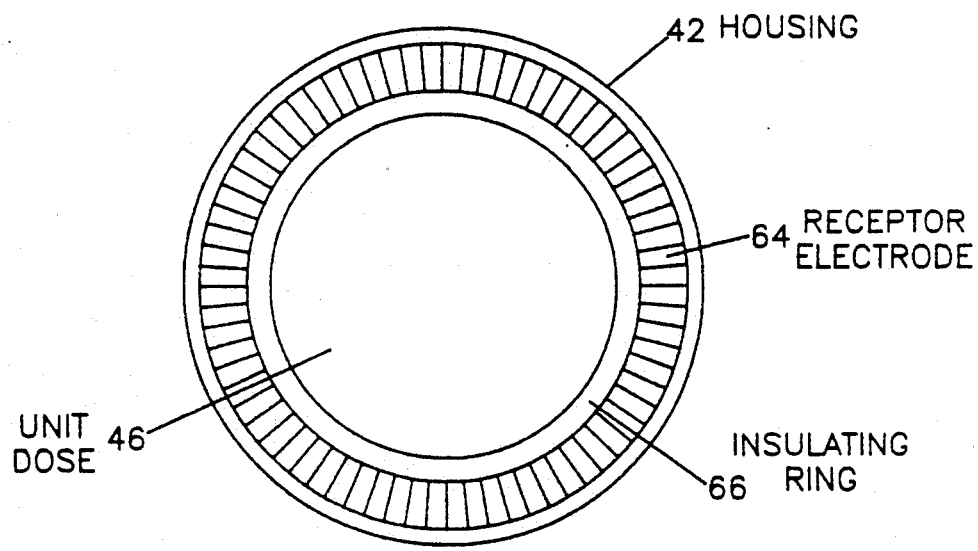
FIG. 2B is a top plan view of said device with the dosage unit in place showing the receptor electrode of said device circumferentially positioned with reference to the installed dosage unit and spaced from said dosage unit by a non-conductive ring.

With respect to the receptor electrode, there will be provided polymer hydrogel discs or other suitable element so as to adapt to the particular iontotherapeutic device utilized. Likewise, the shape will be such that it is adapted for use with the particular receptor electrode utilized by the iontotherapeutic device used. In illustration, FIG. 2B shows the receptor electrode to be in the form of a cylinder that fits within the housing of the iontotherapeutic device in the provided slot and as shown is concentric with the reservoir electrode and spaced therefrom by a non-conductive insulating cylinder, which cylinder is in intimate contact with both the reservoir dosage unit as well as the receptor electrode. Additionally, as shown in embodiment FIG. 3A, it is shown in this wrist-type iontotherapeutic device that the receptor electrode is present in the band surrounding the wrist in a cavity which is on the opposite side of the wrist from the reservoir electrode. Such hydrogeled disc is made in a shape to be secured in the cavity provided in the wrist band.

The following examples are illustrative of the invention but are not intended to be limiting.

EXAMPLE 1

Insulin at a concentration of 100 IU/ml (3.8 mg/ml) is dissolved in an acrylamide buffer solution before the solution is gelled with the addition of an initiator.

The buffer solution used is a pH 3.6 citrate buffer having an ionic strength of 0.1M and is prepared using the following formula:

| Anhydrous citric acid | 26.2 g |
|---|---|
| Disodium hydrogen phosphate | 9.0 g |
| Water. qs to make | 1000 ml |

The buffer is prepared as a stock in double strength, so that allowance remains for the addition of monomers, peptides, and other additives before the volume is made up to the final desired concentration. To this buffer solution, 15% acrylamide (by weight) is added and dissolved. This is followed by the addition of bis-acrylamide (crosslinker) to the acrylamide solution in a concentration of 7% based on monomer weight (1.05% by weight of the total volume of the final solution). Before the addition of insulin, this solution is preserved by the addition of gentamycin sulfate (50 ug/ml) and bacitracin (50 ug/ml). Also, urea is added thereto in a concentration of 2 mg/ml, to minimize adsorption and self-aggregation of the insulin molecule. The catalyst system for polymerizing the monomer (acrylamide) is also added to this solution, delaying the initiator for the final step. The composition of the catalyst system is as follows:

| Ascorbic acid | 0.1% (w/v) |
|---|---|
| Ferrous sulfate | 0.0025% (w/v) |
| Hydrogen peroxide | 0.03% of 30% stock (w/v) |

Insulin is then added to this solution in a concentration of 100 IU/ml (3.8 mg/ml). This solution is then pipetted (150 microliters) into polyethylene tetrafluoride cylindrical molds (having a circular cross section of 10 mm and then it is polymerized in situ by the addition of hydrogen peroxide at a suitable dilution such as to have the requisite concen-tration in 10-15 microliters of dilution. The initiator is added with gentle and brief stirring. Polymerization occurs within about half a minute and very uniform, transparent hydrogel unit dose discs containing the insulin are obtained in the mold. This unit dose is then mounted on the skin in the Valia-Chien cells for in-vitro permeation studies by following the standard procedure as previously referred to.

For permeation study, freshly-excised skin from hairless rats is mounted on the Valia-Chien cells. The device with the exposed side of the hydrogel is placed on the stratum corneum surface of the skin and the donor half-cell remains empty. Current is applied to the other side of the hydrogel using a platinum foil electrode placed on the surface of the hydrogel and iontophoretic delivery is thus accomplished. Samples are taken from the receptor half-cell and are analyzed by radiotracer or radioimmunoassay for extended periods of time.

If desired, aprotinin, a protease inhibitor, can be added to the solution before gelling, in a concentration of about 0.15 mM. This will result in iontophoretic delivery of aprotinin along with insulin and thus will provide protection against proteolytic degradation of insulin in the skin. For the use of the permselective membranes, a Spectra/Por membrane, with a molecular weight cut-off of less than 3,500 can be used to prevent the diffusion of insulin into the first chamber. For the use of ion exchange resins, an appropriate resin in suitable form can be dispersed into the hydrogel matrix in suspension before gelling is carried out.

This procedure can be easily extended to other peptides such as vasopressin or calcitonin or to non-peptide drugs as well.

EXAMPLE 2

The p-HEMA hydrogel is prepared using the following composition:

| | |
|---|---|
| 2-hydroxyethylmethacrylate (HEMA) | 40% |
| Ethylene glycol dimethacrylate (EGDMA) | 0.8% |
| 2,2'-Azo-bix-isobutyronitrile (AIBN) | 0.02% |
| Water | 35% |
| Glycerin | 25% |

The above ingredients are all thoroughly mixed together. AIBN and EGDMA are added in microliter quantities from concentrated stock solutions in ethanol. This mixture of monomer (HEMA), crosslinker (EGDMA), initiator (AIBN), water and plasticizer (glycerin) is then bubbled with nitrogen gas for 20 minutes to remove dissolved oxygen. The solution is then added to polytetrafluoroethylene molds and the filled molds are covered with films. Polymerization is then carried out at 90° C. for 1 hour. Following this, the transparent hydrogel discs are removed from the teflon molds and are extracted with distilled water for 48 hours to remove any residual monomer. Following the extraction pro-cedure, insulin is incorporated into the hydrogel discs by soaking the hydrogel discs in a 0.65 mM solution of insulin in pH 3.6 citrate buffer. The composition of the citrate buffer is the same as given in Example 1. After 24 hours, the hydrogel discs are removed from the insulin solution, wiped free of adhering solution and then placed back into the mold device. Skin permeation studies are then carried out in the same manner as described under Example 1.

EXAMPLE 3

Dose units made following generally the procedures of Examples 1 and 2 are evaluated for their diffusion and permeability using iontophoresis. The following conditions of iontophoresis are used: periodic DC current density of 0.62 mA cm$^2$; square periodic waveform; on/off ratio of 1:1; repetition frequency of 2KHz.

Results of the evaluation are shown in the following Tables:

TABLE 1

A comparison of diffusion coefficients for the release of peptide pharmaceutical from unit doese under iontophoresis.

| Pharmaceutical | Mol. Wt. | Diffusion Coefficient (cm/s) | |
|---|---|---|---|
| | | Polyacrylamide | p-HEMA |
| Insulin | 5808 | $1.32 \times 10^{-6}$ | $5.08 \times 10^{-17}$ |
| Calcitonin | 3418 | $3.80 \times 10^{-6}$ | $8.01 \times 10^{-6}$ |
| Vasopressin | 1084 | $5.42 \times 10^{-6}$ | $1.48 \times 10^{-6}$ |

TABLE 2

A comparison of permeability coefficients for the permeation of peptide pharmaceuticals from unit doses under iontophoresis.

| Pharmaceutical | Mol. Wt. | Permeability Coefficient (cm/s) | | |
|---|---|---|---|---|
| | | Polyacrylamide | p-HEMA | Carbopol |
| Insulin | 5808 | $3.12 \times 10^{-9}$ | $6.54 \times 10^{-9}$ | |
| Calcitonin | 3418 | $6.20 \times 10^{-8}$ | $1.95 \times 10^{-8}$ | $0.69 \times 10^{-8}$ |
| Vasopressin | 1084 | $6.16 \times 10^{-7}$ | $1.06 \times 10^{-7}$ | $2.74 \times 10^{-7}$ |

EXAMPLE 4

Evaluation of dose units made generally following the procedures of Examples 1 and 2 have been made following the iontophoretic procedure and conditions of Example 3. Results of the evaluations are shown in FIGS. 4–13.

What is claimed is:

1. A pharmaceutical reservoir electrode for use in iontotherapeutic delivery of a pharmaceutical which is ionized and is contained therein, comprising:
   a) a housing for said electrode;
   b) a first chamber which contains an electrolytic solution to permit said iontotherapeutic delivery to take place and having present therein ion exchange granules which inhibit increased ionic content through ion generation in the electrode in the first chamber as the iontotherapeutic process takes place;
   c) an electrical terminus to contact electrically the electrolytic solution contained in said first chamber;
   d) a second chamber for receiving a unit dose of said ionized pharmaceutical, and
   e) a permselective membrane separating said first and second chambers, said membrane characterized by having pores with sufficiently low permeability to inhibit substantial passage of said ionized pharmaceutical present in said second chamber into said first chamber, said permselective membrane being substantially free of ion exchange sites.

2. An electrode of claim 1 wherein the unit dose is a crosslinked hydrophilic polymer unit dose adapted to fit into and be securely held in the second chamber, which chamber has an open mouth, said unit dose capable of retaining an aqueous solution of an ionized pharmaceutical and releasing said pharmaceutical by iontotherapeutic process.

3. An electrode of claim 2 wherein said unit dose is a crosslinked acrylamide polymer.

4. An electrode of claim 2 wherein said unit dose is a crosslinked p-HEMA polymer.

5. An electrode of claim 2 wherein said unit dose contains an ionized peptide pharmaceutical.

6. An electrode of claim 5 wherein the polymer of the unit dose is selected from the group consisting of acrylamide polymers and p-HEMA polymers.

7. An electrode of claim 1 wherein the pH of the aqueous solution of said ionized pharmaceutical is at least 1.5 pH units below or above the pKa or isoelectric point, if said ionized pharmaceutical is a peptide.

8. An electrode of claim 7 wherein said pharmaceutical is insulin.

9. An electrode of claim 1 wherein said first chamber is filled with a crosslinked hydrophilic polymer disc which is conductive, filled with an electrolytic buffer and has dispersed therein ion exchange resin granules capable of inhibiting increase of ionic content during iontotherapy.

10. An electrode of claim 9 wherein the unit dose is a crosslinked hydrophilic polymer unit dose capable of retaining an aqueous solution of an ionized pharmaceutical and releasing said pharmaceutical by iontotherapeutic process.

11. An iontotherapeutic device comprising a pharmaceutical reservoir electrode as defined in claim 1.

12. A device of claim 11 wherein said device is capable of providing a periodic DC current having a current density of about 0.1 to about 1 mA/cm$^2$ of area of contact of the electrode with the skin of the subject being treated.

13. A process for iontotherapeutic administration of an ionized pharmaceutical to a subject desiring such therapy, comprising the steps of:
   a) applying to the skin surface of the subject a reservoir electrode as described in claim 1, said reservoir electrode containing an electrolytic solution in the first chamber and containing an ionized pharmaceutical solution in the second chamber;
b) applying to the skin of the subject a second electrode spaced from said first reservoir electrode; and
c) supplying current to the electrode which are electrically connected to cause iontotherapeutic administration of an effective amount of the ionized pharmaceutical to the subject from said first reservoir electrode.

14. A sterile unit dose adapted to be removably inserted into the receiving chamber of a reservoir electrode of a transdermal periodic iontotherapeutic system, said unit dose to be used in electrical contact with intact skin to be iontotherapeutically treated to administer transdermally a systemically effective dose amount of an effective and transdermally absorbable amount of an ionized pharmaceutical; said unit dose containing a sterile solution of said ionized pharmaceutical dispersed therein having an iontotherapeutically effective and physiologically acceptable pH at least about one pH unit lower or higher than the pKa or isoelectric point of said pharmaceutical; said unit dose adapted to permit said pharmaceutical to be released upon application to the reservoir electrode of an effective DC current; said unit dose made of a crosslinked, hydrophilic polymer and being dimensionally stable.

15. A unit dose of claim 14 in which the ionized pharmaceutical is contained and uniformly dispersed in the crosslinked polymer unit dose in which the polymer used in making the unit dose is essentially non-ionic, hydrophilic and essentially compatible with said pharmaceutical and the intact skin to be treated.

16. A unit dose of claim 14 in which the polymer is an acrylamide polymer.

17. A unit dose of claim 14 in which the polymer is a methacrylate type.

18. A unit dose of claim 14 wherein the ionized pharmaceutical is a peptide.

19. A unit dose of claim 18 wherein the pharmaceutical is selected from insulin, vasopressin and calcitonin.

20. A unit dose of claim 18 wherein there is present in said unit dose an effective amount of a proteolytic degradation inhibitor.

21. A unit dose of claim 14 characterized by the water of said aqueous solution of said pharmaceutical has been removed.

* * * * *